United States Patent [19]

Winkler

[11] Patent Number: 5,056,320

[45] Date of Patent: Oct. 15, 1991

[54] PROCESS FOR COOLING AN APPARATUS, DEVICE FOR PERFORMING THE PROCESS, AND REFRIGERATING MACHINE FOR COOLING THE COOLANT PRESENT IN THE DEVICE

[75] Inventor: Norbert Winkler, Nuremberg, Fed. Rep. of Germany

[73] Assignee: Spectron Laser GmbH, Heroldsberg, Fed. Rep. of Germany

[21] Appl. No.: 560,833

[22] Filed: Jul. 31, 1990

[30] Foreign Application Priority Data

Aug. 10, 1989 [CH] Switzerland ............... 02944/89

[51] Int. Cl.$^5$ .............................................. F25D 3/06
[52] U.S. Cl. ......................................... 62/59; 62/237
[58] Field of Search ............... 62/59, 237, 434, 435, 62/233

[56] References Cited

U.S. PATENT DOCUMENTS

| | | | |
|---|---|---|---|
| 1,896,953 | 2/1933 | Hassell | 62/435 X |
| 2,111,905 | 3/1938 | Smith, Jr. et al. | 62/435 X |
| 2,622,923 | 12/1952 | Cobb | 62/59 X |
| 2,825,338 | 3/1958 | Schnepf et al. | 62/237 X |
| 3,507,322 | 4/1970 | Tetrick et al. | 62/237 X |
| 3,545,223 | 12/1970 | Elland | 62/237 |

Primary Examiner—William E. Tapolcai
Attorney, Agent, or Firm—Brady, O'Boyle & Gates

[57] ABSTRACT

A coolant recooler (1) partially filled with a cooling fluid is cooled, in a first process step, to such a low temperature that the thus-produced and stored amount of cold is sufficient for cooling, in a subsequent process step, the coolant of a heat-producing, water-cooled apparatus (4) to be connected, during its operating period. The coolant recooler (1) is movable and connectible, for cooling purposes, to the coolant circuit of the apparatus (4). During the cooling operation, no active refrigerating machine (3) is in operation. After termination of the cooling operation, the coolant recooler (1) is uncoupled from the apparatus (4), transported away, and subsequently its cooling fluid is recooled. The amount of cold still available in each particular case is indicated by a display.

12 Claims, 3 Drawing Sheets

PROCESS FOR COOLING AN APPARATUS, DEVICE FOR PERFORMING THE PROCESS, AND REFRIGERATING MACHINE FOR COOLING THE COOLANT PRESENT IN THE DEVICE

The invention relates to a process for cooling an apparatus to a device for performing the process and to a refrigerating machine for cooling the coolant present in the device.

Appliances producing large amounts of heat are normally cooled with (distilled or deionized) water which is cooled in a so-called cooling water recooler. The cooling water recooler comprises, for cooling the coolant, a cooling unit with a motor compressor and an air-cooled condenser, the heat of which is passed on to the surroundings by way of a blower, and a heat exchanger wherein the water is cooled by the coolant. The blower air is withdrawn from the surroundings. The air inlet and outlet are covered by a screen to protect from the blower.

The blower and the compressor generate noise and vibrations. Furthermore, the blower heats the surrounding air and causes turbulences in the latter.

When utilizing, for example, a laser cooled by means of a cooling water recooler in an operating room for retina coagulation, for the irradiation of wounds or of cancer-riddled tissue, during operations, etc., the stirred-up dust and the difficulties encountered in disinfecting the air inlet and outlet means and the entire air circuit within the cooling water recooler represent a danger to the patient; furthermore, the generation of heat and the noise of the cooling water recooler are a disturbance. In order to avoid these, the cooling water recooler had to be located in another room and correspondingly long cooling conduits had to be used. Since the deployment site of the laser must be variable, these cooling conduits then lie, as flexible hoses, around the floor of the operating room and constitute "booby traps".

The invention is to provide a remedy in this connection. The invention, as characterized in the claims, solves the problem of creating a method for cooling an apparatus avoiding any stirring up of dust, vibrations, and any kind of noise during the cooling step, as well as of providing a device which can be sterilized in a simple way and can be coupled to the apparatus to be cooled by means of short connections.

Embodiments of the process of this invention, of the device and of the refrigerating machine will be described in greater detail below with reference to the drawings wherein.

Figure 1:
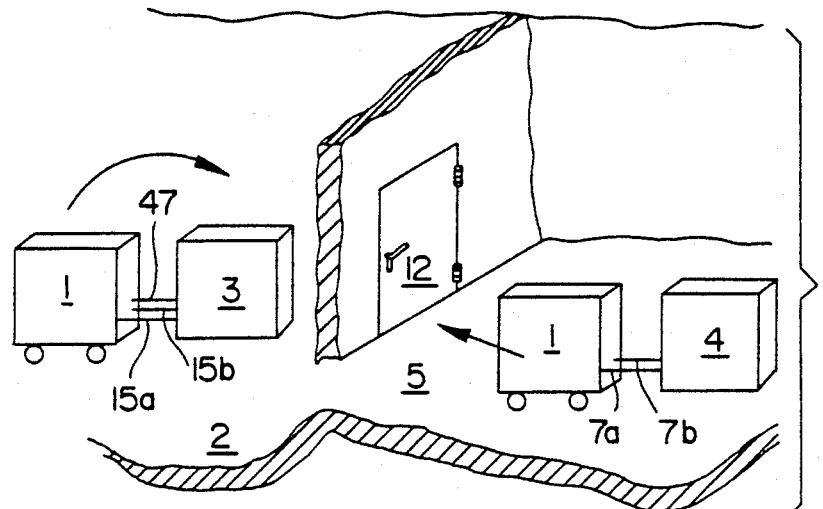
FIG. 1 shows a device first connected to a cooling machine in a make-ready station and then, after being transported to a heat-producing device, to the latter.

In FIG. 1, the device of a movable coolant recooler 1 is connected to a refrigerating machine 3 in a left-hand room as the make-ready station 2 and to a heat-producing system 4 to be cooled, in a right-hand room 5. The coolant recooler 1 can be pushed, through a door 12 to be opened, from the make-ready station 2 to room 5.

Figure 2:
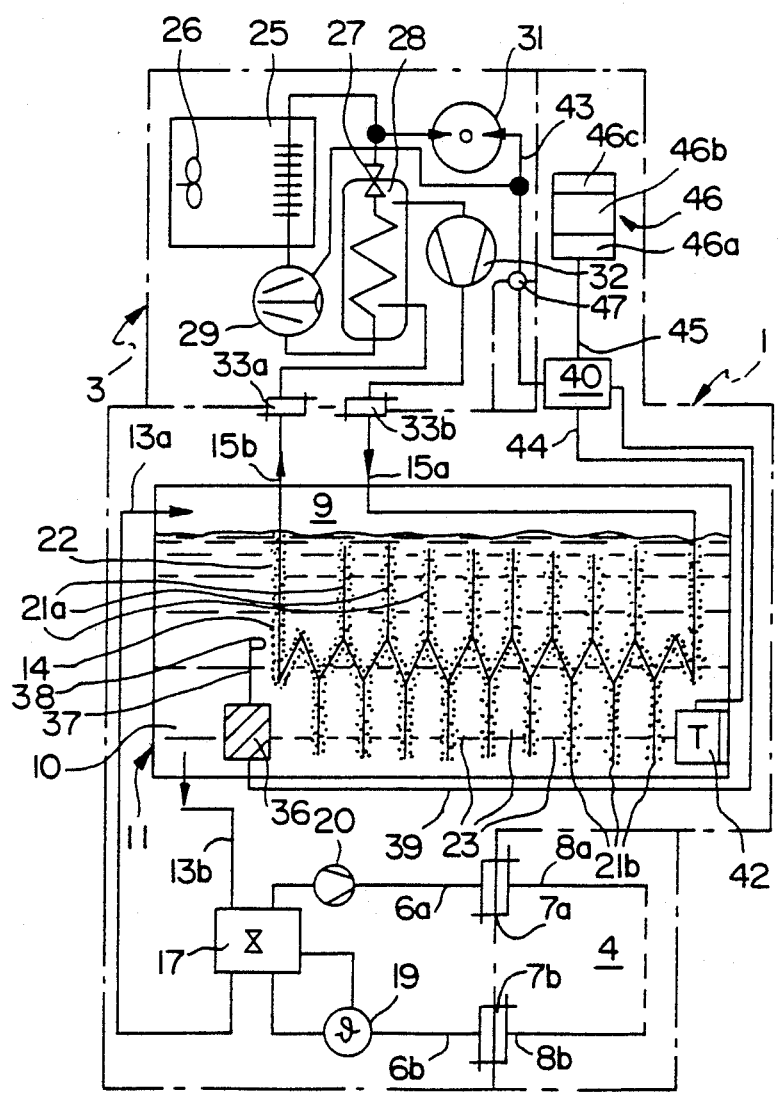
FIG. 2 is a block circuit diagram of the device for cooling the apparatus.

The coolant recooler 1 has a thermally insulated cold storage means 11 filled partially with a coolant 10 as illustrated in FIG. 2. The coolant 10 is cooled, as described below, by means of the refrigerating machine 3; after adequate cooling, the coolant recooler 1 is detached from the refrigerating machine 3, moved into the room 5 where the system 4 is located, and the cooling water circuit of the latter is connected to the coolant recooler 1. The cooling water of the system 4 is thus cooled by the coolant recooler 1. After one to two hours, depending on the amount of heat to be removed, the cooling fluid 10 then has heated up to such an extent that no additional heat can be absorbed. Then the coolant recooler 1 with the heated coolant 10 is moved back into the make-ready station 2, reconnected to the refrigerating machine 3, and a new coolant recooler 1 with cold coolant 10 is connected to the system 4.

In FIG. 2, the coolant recooler 1 is shown connected to the refrigerating machine 3 and to the system 4, in a schematic view. This combination has been used merely for simplifying the illustration: In the make-ready station 2, as depicted in FIG. 1, the coolant recooler 1 is connected only to the refrigerating machine 3 and, during cooling of the system 4 in room 5, is connected only to the latter. The coolant recooler 1 is connected by way of a coolant feed conduit and coolant return conduit 6a and 6b, respectively, via respectively one quick-action coupling 7a and 7b to respectively one coolant feed conduit and coolant return conduit 8a and 8b of the apparatus 4.

The coolant recooler 1 comprises the heat-insulating container 11 as a regenerator, filled almost completely with the coolant 10, except for an air cushion 9, a liquid inlet means and a liquid discharge means 13a and 13b, respectively, terminating into this container; a cooling coil 14 as a heat exchanger, the inlet and discharge conduits 15a and 15b of which being connectible to the refrigerating machine 3; and a three-way mixer 17 connected to the liquid inlet means and a liquid discharge means 13a and 13b, respectively, as well as to the feed and return conduits 6a and 6b, this three-way mixer being controlled by way of a temperature sensor 19 as the temperature setting member in the return conduit 6b. A pump 20 for the coolant 10 is arranged between the three-way mixer 17 and the instant coupling 7a in the feed conduit 6a. The pump 20 propels the coolant 10 through the feed and return conduits 6a and 6b, as well as through the liquid inlet necessary in order to be able to compensate for thermal expansions of the coolant 10, as well as changes in volume during its solidification.

The surface area of the cooling coil 14 arranged within the container 11 is enlarged by outjutting heat-conducting baffles 21a and 21b which are blanketed with a thick layer 22 of ice during a cooling step, described below, in the make-ready station 2, the cooling coil 14 likewise being covered with this ice layer which then thaws gradually during the step of giving off cold in the room 5 with the system 4 being connected. The spacing of the baffles 21a and 21b from each other is chosen so that the space 23 located therebetween is not filled up entirely with ice 22 in order to avoid mechanical stress due to ice formation.

The refrigerating machine 3 has a condenser 25 wherein its refrigerant, usually "Freon", is condensed; the heat of condensation of the condenser being removed by means of a fan 26; an injection valve 27; a heat exchanger 28; a compressor 29; and a pressure gauge 31 for monitoring the pressure of the refrigerant.

In heat exchanger 28, the refrigerant "Freon" cools the heat-transfer medium glycol, the point of solidification of which is lower than that of water. The cooled glycol is propelled through the cooling coil 14 by means of a further pump 32 in the refrigerating machine 3.

The two inlet and discharge conduits 15a and 15b can be cut off by respectively one instant coupling 33a and 33b in order to be able to sever the refrigerating machine 3 from the coolant recooler 1 after adequate cooling of the coolant 10 in container 11.

As schematically illustrated in FIG. 2, a mechanical switch 36 is utilized for measuring the thickness of the ice layer 22. The switch 36 has a lug 37 with a thickened outer end 38. The end 38 presses resiliently against the surface of the cooling coil 14. If ice 22 is formed, this ice urges the end 38 away from the surface. Once the end has been pressed away by a preset distance, a mechanical contact is closed.

The switch 36 is connected by way of a line 39 to an evaluating circuit 40. The container 11 houses, in addition to the switch 36, a temperature gauge 42 which is likewise connected to the evaluating circuit 40 via an electrical line 44. The evaluating circuit 40 is furthermore connected via a further electric wire 43 to pressure gauge 31, the electric wire leading also to the compressor 29.

Via a line 45, the evaluating circuit 40 controls a display 46.

As described further below, the accumulation of ice 22 can be determined by way of a pressure measurement in the refrigerant cycle of "Freon" by means of the pressure gauge 31 since owing to an increasing ice layer 22 the amount of cold given off in the heat exchanger 14 is reduced and thereby the pressure rises in the refrigerant circuit.

The refrigerating machine 3 and the coolant recooler 1 are units that can be separated from each other owing to the quick-action couplings 33a and 33b and due to an electrical plug 47 in the line 43. The coolant recooler 1 is movable. The refrigerating machine 3 is located in the make-ready station 2 and there is coupled to the coolant recooler 1. The make-ready station 2 is fashioned so that noise and heat produced by the compressor 29, the fan 26, and the pump 32 will not interfere.

During the cooling step in the make-ready station 2, "Freon" as the refrigerant is compressed by the compressor 29 and cooled in condenser 25 by means of surrounding air taken in by the fan 26. The thus-cooled "Freon" is expanded directly upstream of heat exchanger 28 in an injection valve 27 whereby it is further cooled. In heat exchanger 28, temperature equalization is achieved between the "Freon" refrigerant circuit and the cold transfer medium circuit of the glycol. Thereby, the glycol is cooled down to about −10° C. The thus-cooled glycol is pumped by pump 32 through the cooling coil 14 of the coolant recooler 1 and thereby the water 10 in container 11 is cooled off.

Cooling of the water 10 in container 11 proceeds until an ice layer 22 having a thickness of several centimeters has formed on the cooling coil 14 and on the baffles 21a and 21b, connected to the coil in a thermally well-conductive fashion. Since ice displays a very poor heat conductivity, the amount of cold produced by the refrigerating machine 3 can no longer be given off via the glycol. Thereby, the pressure in the "Freon" circulation, measured by the pressure gauge 31, increases. Upon attainment of a preset pressure, the compressor 29 is shut off via the electrical wire 43 and a signal is transmitted to the evaluating circuit 40.

During the growth of the ice layer 22, the end 38 of switch 36 is likewise located at an increasing distance from the surface of the cooling coil 14; also, the temperature in the container is continuously measured by means of the temperature gauge 42. The ice layer 22 accumulates, owing to the above monitoring process, only to such a thickness that in all cases a space 23 between the baffles 21 remains free of ice. This ensures that only negligible mechanical forces act on the cooling coil 14 on account of the ice formation. Volume changes during cooling and later on during the warming up of the coolant 10 are compensated for by the air cushion 9.

Upon shutoff of the compressor 29 based on the pressure rise in the "Freon" circuit, an optimum amount of cold is stored in container 11. The volume of container 11 and also the surface area of the cooling coil 14 and of the baffles 21a and 21b are dependent on the required amount of refrigeration for cooling the coolant 10 of the heat-producing apparatus 4. With the use of about 200 liters of coolant plus ice, about ten kilowatt hours of heat can be removed.

Figure 3:
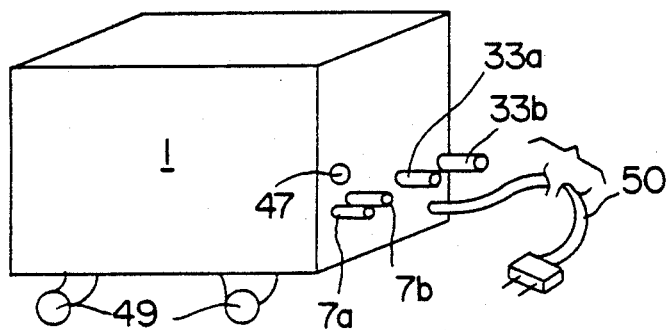
FIG. 3 is a perspective view of the device.

For effecting transport from the make-ready station 2 to room 5, the instant couplings 33a and 33b and the plug 47 between the refrigerating machine 3 and the coolant recooler 1 are released, and the coolant recooler 1 is moved by means of its four casters 49, two of which are depicted in FIG. 3. The baffles 21a and 21b in container 11 serve not only for enlarging the surface area of the cooling coil 14 but also as so-called surge baffles in order to extensively suppress sloshing to and fro of the unsolidified water in container 11 during transport.

After an optional disinfection, the coolant recooler 1 is moved into the room 5, for example into an operating room, in order to be connected to a laser to be employed therein, for cooling the laser coolant. Disinfection of the coolant recooler 1 can be achieved in a simple way since this recooler has only smooth paneling; there is no "radiator grille" as in the known coolant water recoolers any more.

In room 5, the coolant recooler 1 is connected by means of the instant couplings 7a and 7b to the coolant feed and return conduits 8a and 8b of the apparatus 4 and connected via a mains cable 50 to the current supply. An electric current connection is required for operating the pump 20, the three-way mixer 17, the evaluating circuit 40, the display 46, the switch 36, and the temperature measurement by the temperature sensors 19 and 42.

The pump 20 propels the coolant 10 into the apparatus 4, and the temperature sensor 19 measures the coolant temperature in the return conduit 6b. Depending on the thus-determined temperature, a greater or lesser amount of cold coolant 10 is admixed through the three-way mixer 17 from container 11.

At the beginning of the cooling process, the maximum amount of cold is stored in the container and thus the thickness of the ice layer 22 monitored by the switch 36 is largest, and the temperature of the coolant 10 measured by the temperature gauge 42 is at the lowest point. The thickness of the ice and the temperature are monitored by the evaluating circuit 40 and indicated by means of the display 46 comprising three display areas 46a, 46b and 46c. The area 46a lights up in case of a coolant temperature of below 5° C. and with an ice layer 22 being present. The indicator area 46b lights up in case such an amount of cold has already been withdrawn that the ice layer 22 has disappeared, but the coolant temperature is still below 10° C., and the display field 46c lights up in case the coolant temperature measured by the temperature gauge 42 exceeds 10° C. Illumination of the display area 46c means a danger signal since the quantity of cold still available is highly limited. The lighting up of the display field 46c can also be coupled with an acoustic alarm sound.

The coolant recooler 1 still in operation is decoupled, in a proper operating pause, as soon as possible; a new coolant recooler 1 is connected to the apparatus 4, and the uncoupled coolant recooler 1 is rolled back to the make-ready station 2 and connected to the refrigerating machine 3.

Figure 5:
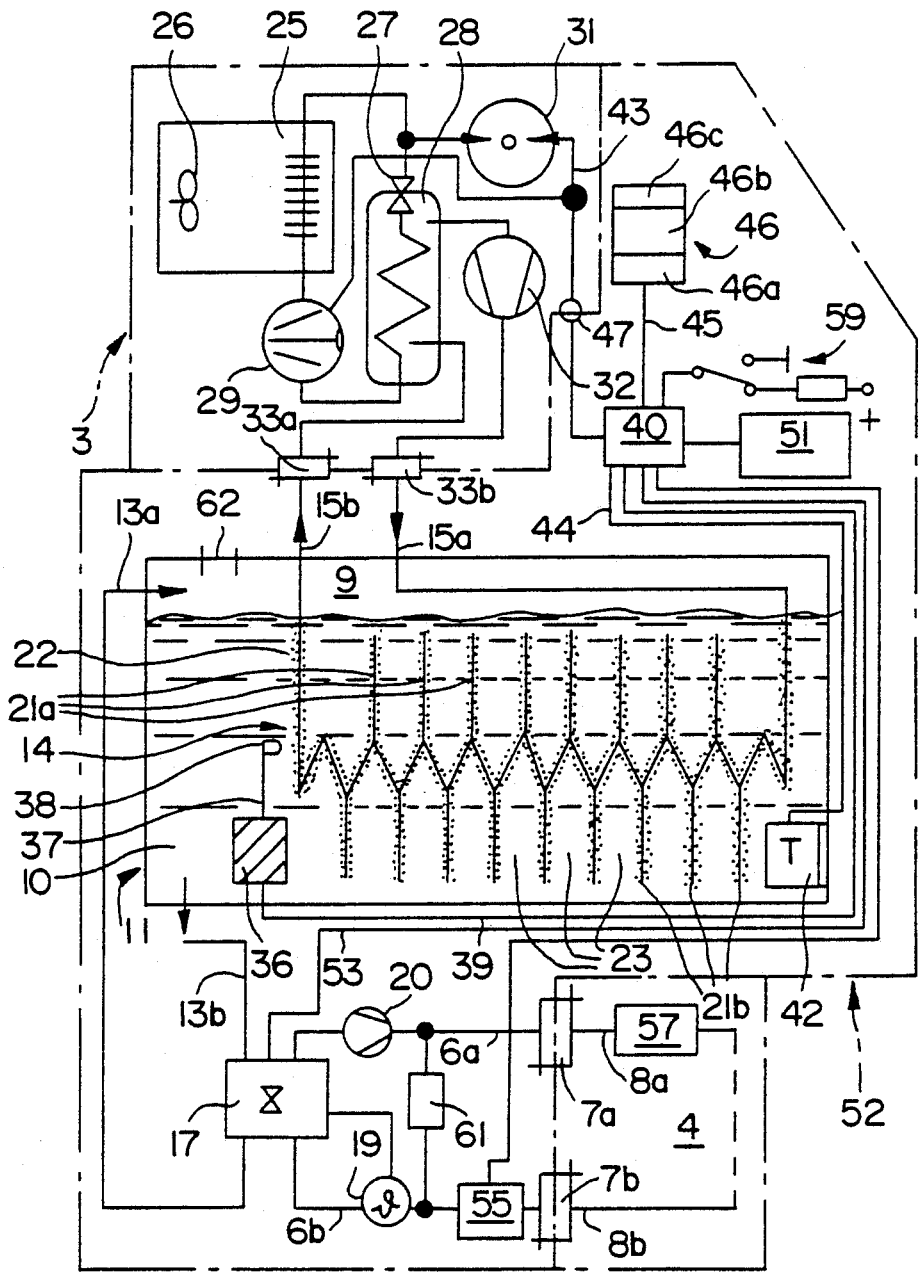
FIG. 5 is a variation of the device shown in FIG. 2.

Instead of controlling the three-way mixer 17 only by way of the temperature sensor 19, it can be additionally controlled by a timing member 51 via the evaluating circuit 40, as in a variation 52 of the cooling recooler 1 illustrated in FIG. 5. The three-way valve 17 receives an electrical signal from the evaluating circuit 40 via an electrical connection 53; this signal acts so that the three-way valve 17 connects the coolant conduit 13b completely to the feed conduit to the pump 20 and the return conduit 6b completely to the return conduit 13a during the time set by the timing member 51. The coolant 10 thus is conducted into the apparatus 4 by way of the pump 20, and the coolant 10 heated up in the apparatus 4 is returned into the container 11. There is no intermixing of cold coolant 10 from container 11 and coolant 10 heated in the apparatus 4. Consequently, air contained in the coolant conduits 6a, 6b, 8a, 8b, as well as in components, not shown, connected to these conduits in the apparatus 4, is conveyed directly into the container 11 and is collected in the air cushion 9 of the latter. The conveying power of the pump 20 is not impaired by the air from the apparatus 4. The time set with the timing member 51 is selected so that the air is driven entirely out of the apparatus 4. Sixty seconds are sufficient in case of the customary equipment to be cooled, such as, for example, medical lasers. After this time period, the three-way valve 17 is set by the temperature sensor 19 as described above. The air that has accumulated in the air cushion 9 can be discharged by way of a refilling and vent opening 62, and coolant 10 can also be replenished.

As illustrated in FIG. 5, a coolant reflux monitor 55 can additionally be installed in the return conduit 6b, this monitor being connected to the evaluating circuit 40. If the coolant reflux monitor 55, after elapse of the time set with the timing member 51, does not signal any reflux of coolant, then the three-way valve 17 is not switched over to mixing based on the temperature measured by the temperature sensor 19. If there is still no coolant reflux after a total of three minutes, the pump 20 is switched off.

There are apparatuses 4 which comprise a primary coolant circuit cooling the heat-producing structural parts, and a secondary coolant circuit with the feed and return conduits 8a and 8b, this secondary coolant circuit cooling the coolant of the primary coolant circuit by way of a heat exchanger, not shown. The coolant flow of the secondary coolant circuit is turned on and off as required by means of a valve, preferably a solenoid valve 57. With the solenoid valve 57 being closed, the coolant reflux monitor 55 does not measure any coolant reflux and thus would cut off the pump 20 after three minutes. In order to prevent shutoff of the pump 20, the evaluating circuit 40 is connected to a selector switch 59. If the selector switch 59 is set so that its connection with the evaluating sircuit 40 is at positive potential, then the effect of the coolant reflux monitor 55 is suppressed; at ground potential, the coolant reflux monitor 55 is operative. In case of apparatuses 4 wherein a secondary coolant circuit is turned on and off with a solenoid valve 57, the selector switch 59 is set at positive potential. The pump 20 is designed so that it can work even with the solenoid valve 57 being closed, without incurring any damage.

It is also possible to install a pressure monitor 61 between the coolant conduits 6a and 6b; this monitor, when a set lower pressure difference threshold between the coolant conduits 6a and 6b is passed in the downward direction, activates the pump 20 and deactivates the pump again when an upper pressure difference threshold is exceeded.

Figure 4:
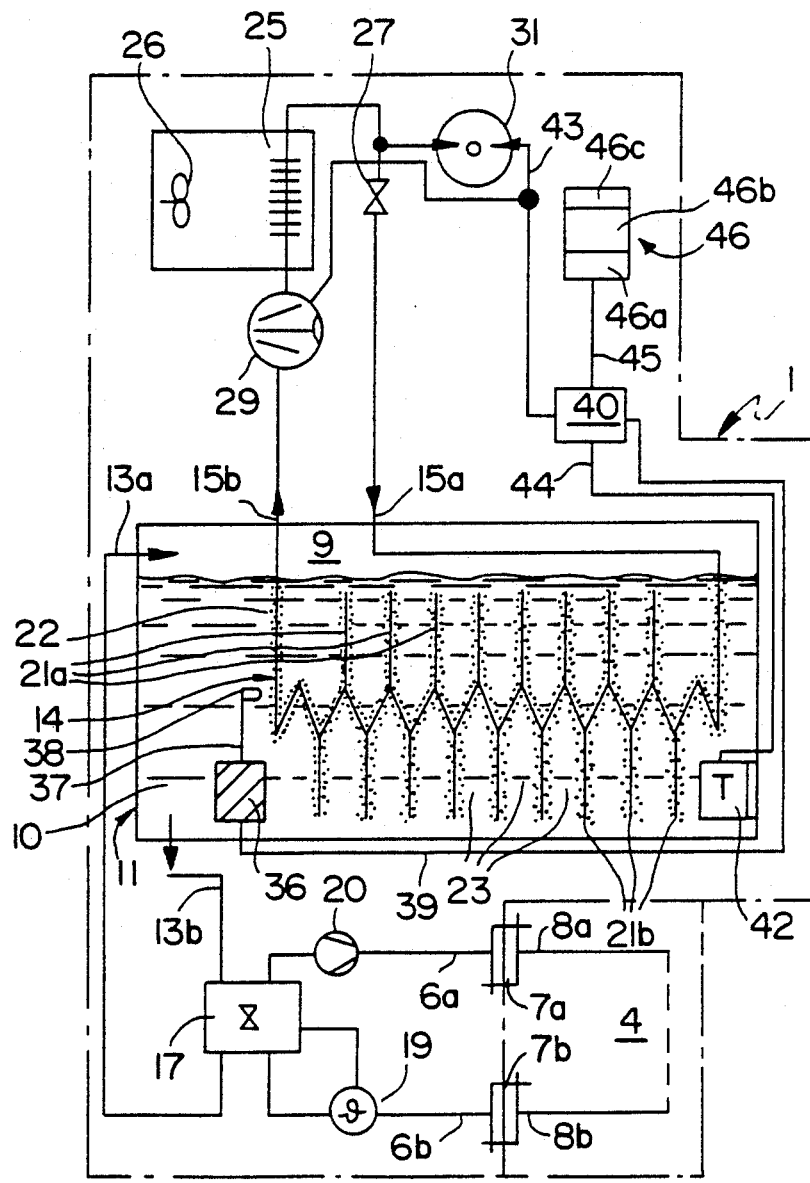
FIG. 4 is a block circuit diagram of a variation of the device.

Instead of installing the refrigerating machine 3 in the make-ready station 2, it can also be integrated into a unit together with the coolant recooler 1, as illustrated in FIG. 4. For the reasons mentioned above, only the coolant recooler 1 is then in operation during the cooling of apparatus 4. The entire unit, after cooling has been completed, is moved out of room 5 and can then be connected to any desired wall outlet in order to render it ready for operation for the subsequent usage.

In contrast to the above-described embodiment, each coolant recooler 1 herein is equipped with a refrigerating machine 3. In this version, however, the heat exchanger 28, the pump 32, the quick-action couplings 33a and 33b, and the plug are omitted. The injection valve 27 is in this case arranged directly at the inlet to the cooling coil 14, and the cooling coil 14 is traversed, in place of glycol, directly by "Freon". This arrangement is utilized with advantage in case of only one or two coolant recoolers 1 to be employed, but it has the drawback of being more difficult to disinfect.

Normal tap water, distilled water, or water with additives is utilized as the coolant 10, depending in the characteristics of the heat-producing apparatus 4. Disinfecting additives have the advantage that contamination of the cooling conduits 6a, 6b, 8a, 8b, 13a, and 13b, as well as of the instant couplings 7a and 7b and of the cooling coil 14 is prevented. Also, with additives which lower the freezing point, a greater amount of cold can be stored in a given volume of the container 11.

Instead of a refrigerating machine 3 with compressor 29, it is also possible to utilize a refrigerating machine with an evaporator, operable with a gas, for example.

The pressure gauge 31 can also be mounted in the coolant recooler 1 at the inlet conduit 15a instead of upstream of the injection valve 27 in the refrigerating machine 3. However, a more compact structural design can be obtained with installation in the refrigerating machine 3.

With the above-described process for cooling the coolant 10 of a heat-producing apparatus 4 by means of a coolant recooler 1, the heat-removing process thereof is locally separated from the apparatus 4 to be cooled whereby all of the inconveniences, such as production of heat and noise, are moved to a different site. Since heat need no longer be discharged immediately into the surroundings, the coolant recooler 1 is designed as an enclosed device which, on the one hand, can be easily disinfected but, on the other hand, can also be very readily protected against splash water and strong dust accumulation. Also, the coolant recooler 1 can be recharged during times when electrical energy is cheaply available.

I claim:

1. A process for cooling an apparatus having an inlet and an outlet for a coolant, comprising the steps of cooling a coolant of a movable coolant storage means at a make-ready station, said movable coolant storage means having an outlet and an inlet for the coolant, transporting said storage means to said apparatus, connecting the inlets and outlets of said apparatus and said storage means, pumping said coolant from said storage means to said apparatus and mixing the coolant flowing back from said apparatus with the coolant from said storage means in such a proportion that the mixture supplied to the apparatus has a predetermined temperature, detaching after a period of operation said storage means from said apparatus, and transporting said storage means back to said make-ready station for a re-cooling of the coolant.

2. A process according to claim 1, including cooling the coolant of said storage means in said make-ready station to its solidification temperature, measuring the thickness of the growing solid sheet inside said storing means, and stopping the cooling process when the solid sheet has a predetermined thickness.

3. A process for cooling an apparatus having an inlet and an outlet for a coolant, comprising the steps of cooling a coolant of a movable coolant storage means at a make-ready station, said movable coolant storage means having an outlet and an inlet for the coolant, transporting said storage means to said apparatus, connecting the inlets and outlets of said apparatus and said storage means, circulating said coolant between said storage means and said apparatus during a settable time, after said settable time mixing the coolant flowing back from said apparatus with the coolant from said storage means in such a proportion that the mixture supplied to the apparatus has a predetermined temperature, detaching after a period of operation said storage means from said apparatus, and transporting said storage means back to said make-ready station for a re-cooling of the coolant.

4. A process according to claim 3, including cooling the coolant of said storage means in said make-ready station to its solidification temperature, measuring the thickness of the growing solid sheet inside said storing means, and stopping the cooling process when the solid sheet has a predetermined thickness.

5. A process for cooling an apparatus having an inlet and an outlet for a coolant, comprising the steps of cooling a coolant of a movable coolant storage means at a make-ready station, said movable coolant storage means having an outlet and an inlet for the coolant, transporting said storage means to said apparatus, connecting the inlets and outlets of said apparatus and said storage means, pumping said coolant from said storage means into said apparatus for circulation of the coolant between the storage means and apparatus, and turning off said pumping if after a predetermined time no coolant flows back from said apparatus.

6. A process according to claim 5, including cooling the coolant of said storage means in said make-ready station to its solidification temperature, measuring the thickness of the growing solid sheet inside said storing means, and stopping the cooling process when the solid sheet has a predetermined thickness.

7. A device for cooling an apparatus to be cooled by a coolant mixture comprising, a movable coolant storage means having a container at least partially filled with a coolant and an outlet and inlet for the coolant, a heat exchanger means in said container for cooling the coolant, said heat exchanger means having input and output connecting means for connecting the heat exchanger means to a refrigeration unit in a make-ready station, a mixing valve connected by first conduits to said container and connected by second conduits to said outlet and inlet, said mixing valve being operable to mix coolant from said container with coolant flowing back from the apparatus to be cooled through said inlet, and means connected with said mixing valve to circulate the coolant mixture through said outlet to the apparatus to be cooled.

8. Device according to claim 7, in which said mixing valve is a mixing control valve, a temperature measuring means connected with said second conduits, said temperature measuring means is connected with said mixing control valve, said mixing control valve being controlled by said temperature measuring means to mix the coolant from said container with the coolant flowing back from the apparatus to be cooled through said inlet in such a way, that the coolant flowing out of said outlet to the apparatus to be cooled has a predetermined temperature.

9. A device for cooling an apparatus to be cooled by a coolant comprising, a movable coolant storage means having a container at least partially filled with coolant and an outlet and an inlet for the coolant, a heat exchanger means in said container for cooling the coolant, said heat exchanger means having input and output connecting means for connecting the heat exchanger means to a refrigeration unit in a make-ready station, a pump connected for pumping said coolant out of said outlet, a control circuit connected for controlling said pump and having a timing member setting a time period, a flow measuring unit connected to measure the flow of coolant incoming through said inlet and connected to said control circuit, and said control circuit operable to stop said pump, when at the end of said time period beginning with starting of the pump said flow measuring unit indicates no coolant flow.

10. Device according to claim 9, including a heat exchanger tubing in said container for cooling the coolant, said heat exchanger tubing having input and output connecting means for connecting the tubing to a refrigeration unit in a make-ready station.

11. A device for cooling an apparatus to be cooled by a coolant comprising,
   a movable coolant storage means having a container at least partially filled with a coolant and an outlet and an inlet for the coolant,
   a heat exchanger tubing arranged in said container for cooling the coolant in said container,
   said heat exchanger tubing having input and output connecting means for connecting the tubing to a refrigeration unit in a make-ready station,
   said heat exchanger tubing having heat-conducting baffles thereon projecting away from the tubing and being arranged so that they impede the sloshing to and fro of the coolant in the container during transportation of the movable coolant storage means.

12. Device according to claim 7, including a timing member (51) which acts on the mixing valve (17) in such a way that it conducts, during a settable time period, the coolant (10) from said container 11) into the apparatus to be cooled (4) without admixture of the coolant (10) returning from the apparatus to be cooled (4).

* * * * *